US010520405B2

(12) United States Patent
Im

(10) Patent No.: US 10,520,405 B2
(45) Date of Patent: Dec. 31, 2019

(54) APPARATUS FOR PROVIDING OBJECT TO BE MEDICALLY EXAMINED BY BLOWING

(71) Applicant: Biodyne Co., Ltd., Gyeonggi-do (KR)

(72) Inventor: Wook Bin Im, Seoul (KR)

(73) Assignee: Biodyne Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/290,774

(22) Filed: Mar. 1, 2019

(65) Prior Publication Data
US 2019/0195755 A1 Jun. 27, 2019

Related U.S. Application Data

(63) Continuation of application No. 14/770,386, filed as application No. PCT/KR2014/000129 on Jan. 7, 2014, now abandoned.

(30) Foreign Application Priority Data

Feb. 26, 2013 (KR) .......................... 10-2013-0020723

(51) Int. Cl.
G01N 1/38 (2006.01)
G01N 1/28 (2006.01)
G02B 21/36 (2006.01)
G01N 1/31 (2006.01)

(52) U.S. Cl.
CPC ............. *G01N 1/38* (2013.01); *G01N 1/2813* (2013.01); *G02B 21/362* (2013.01); *G01N 2001/317* (2013.01); *G01N 2001/387* (2013.01)

(58) Field of Classification Search
CPC ....................................................... C12M 33/14
See application file for complete search history.

(56) References Cited

U.S. PATENT DOCUMENTS

| 4,395,493 | A | 7/1983 | Zahniser et al. |
| 5,240,606 | A | 8/1993 | Lapidus et al. |
| 5,269,918 | A | 12/1993 | Lapidus et al. |
| 8,119,399 | B2* | 2/2012 | Duhamel ............. G01N 1/2813 210/348 |
| 8,396,669 | B2 | 3/2013 | Cocks et al. |
| 2008/0142456 | A1 | 6/2008 | Duhamel et al. |
| 2016/0003719 | A1 | 1/2016 | Im |

FOREIGN PATENT DOCUMENTS

| CN | 102154096 | 8/2011 |
| CN | 102759472 | 10/2012 |
| CN | 105008892 | 10/2015 |
| EP | 2963411 | 1/1916 |
| EP | 0465832 | 10/1998 |
| EP | 2388567 | 11/2011 |
| JP | 2016514256 | 5/1916 |
| JP | H10104136 | 4/1998 |

(Continued)

*Primary Examiner* — Justin N Olamit
(74) *Attorney, Agent, or Firm* — Perkins Coie LLP

(57) ABSTRACT

An apparatus for providing an object to be medically examined by blowing is provided where air is blown into a container in which an object to be medically examined is stored, so as to make the uniform distribution state of the object to be medically examined from the inside of the container, thereby ensuring the sameness of the object to be medically examined, which is to be extracted from the container.

11 Claims, 11 Drawing Sheets

(56) References Cited

FOREIGN PATENT DOCUMENTS

| | | |
|---|---|---|
| JP | 2005241423 | 9/2005 |
| JP | 2009025027 | 2/2009 |
| KR | 20020041172 | 6/2002 |
| KR | 20050100475 | 10/2005 |
| KR | 100660117 | 12/2006 |
| KR | 20070095810 | 10/2007 |
| KR | 20110061143 | 6/2011 |
| KR | 101058409 | 8/2011 |
| KR | 101094249 | 12/2011 |
| KR | 101317311 | 10/2013 |
| RU | 2015140992 | 3/1917 |
| WO | WO2014133259 | 9/2014 |

* cited by examiner

APPARATUS FOR PROVIDING OBJECT TO BE MEDICALLY EXAMINED BY BLOWING

CROSS REFERENCE TO RELATED APPLICATIONS

This application is a continuation of U.S. application Ser. No. 14/770,386, filed Aug. 25, 2015, which is a 371 National Phase of PCT/KR2014/000129, filed Jan. 7, 2014, which claims priority to KR Application No. 10-2013-0020723, filed on Feb. 26, 2013, all of which are hereby incorporated by reference in their entireties.

BACKGROUND OF THE INVENTION

1. Field of the Invention

The present invention relates to an apparatus for placing objects to be examined (examination objects) by blowing, configured in such a way as to: blow air into a container in which the examination objects are stored, so that the examination objects are spread in a uniform distribution state in the container, thereby ensuring the sameness of the examination objects to be extracted for examination.

2. Description of the Related Art

In order to inspect objects such as cells, etc. through inspection instruments such as a microscope, etc., a preset quantity of objects must be placed on the slide. To this end, according to convention art, objects are applied onto the slide with a brush.

In addition, an instrument has been developed that can collect content by using a piston. A solution tube and a cell inspection instrument according to conventional art are described as follows. The conventional solution tube is used to mix cells, such as cervical cells, etc., collected by a picking tool, in solution in order to inspect the cells. The solution tube is configured as a container that places the picking tool that has collected cells in the inside and is closed with a cap. The solution tube requires a shaking operation to mix the cells with solution, which is performed by a user's hand operation or other devices. The solution tube is restricted to be used for storing solution. Therefore, conventional instruments for transferring cells onto a slide have been equipped with an additional container for storing solution. That is, conventional instruments need additional containers as well as the solution tube.

In particular, the container of the conventional instrument for storing solution is configured to be open in the upper part, so that the solution will unavoidably be exposed to air. In addition, the cylinder-type body supports a filter on which a collecting membrane is placed and the piston moving out of/into the body sucks solution from the container. The body and container are coupled to each other by screws.

Conventional art has an additional solution tube for spreading cells, smeared over a brush, to the solution, and operates in such a way that: the solution tube is shaken so that cells are sufficiently spread in the solution; the solution with cells is poured into another container; a suction tool sucks the solution while it is tightly attached to the bottom of the filter; and the cells filtered by the filter are rubbed and collected on the slide.

However, when the container is separated from the body in order to move the collecting membrane close to the slide, the mixed solution remaining in the container is poured down and useless due to gravity. That is, remaining mixed solution cannot be re-used and may, if re-used, be insanitary.

In addition, when solution is poured in a container and then a preset amount of solution is sucked through a suction tool, the solution remaining in the container is already exposed to air, and thus does not guarantee, if it is re-used for inspection, the accuracy of the inspection.

In addition, the conventional instrument is disadvantageous in that, since users need to, manually, step by step, perform the process of transferring cells from the solution tube to the slide, the process: takes a relatively long time to complete; may transfer contaminants or impurities from the user's hands to the slide; places non-uniform amounts of objects on the slide, overlapping on the slide, which decreases the accuracy of the inspection; and may damage the objects.

The conventional technology related to the present invention is Korean Patent No. 10-1058409.

SUMMARY OF THE INVENTION

The present invention has been made in view of the above problems, and provides an apparatus for placing objects to be examined, configured so that the automatic means separates objects from a container containing a mixed solution including objects to be examined (examination objects), such as cells, etc., and allows the slide to collect the examination objects.

The present invention further provides an examination object placing apparatus that blows, in the process of sucking and extracting objects from a container, air to the objects, thereby forming a uniform distribution state for the samples in the container.

In order to achieve the objectives of the present invention, the present invention provides an apparatus for placing objects to be examined (examination objects) by blowing, comprising: a container fixing means for holding a container, wherein the container is equipped with a first cap filter at the opening and contains a mixed solution with the examination objects; a suction unit with an air ejecting and sucking means, wherein the air ejecting and sucking means: is coupled to a filter for letting a solution through and blocking the examination objects, in a state where the opening of the container containing the mixed solution is coupled to the upper end of the filter; firstly ejects air to the lower side of the filter to float the examination objects in the container; and then secondly performs a suction operation to place the examination objects inside the container on the filter; a blower unit for generating, when a slide is located on the upper end of the filter on which the examination objects are placed, positive pressure in the lower end of the filter and placing the examination objects placed on the filter onto the slide; and a filter transfer means for sequentially transferring the filter onto the suction unit and the blower unit. The suction unit: is coupled to the filter in a state where the opening of the container is coupled to the filter; firstly expels air to the filter so that the examination objects, settled in the first cap filter of the container, are floated and uniformly spread in the mixed solution; secondly sucks the examination objects from the container; and places the examination objects on the filter.

In order to achieve the objectives of the present invention, the suction unit: secondly sucks the filter; moves down with the filter after the examination objects are placed on the filter to separate the filter from the opening of the container;

additionally sucks a solution and materials hindering the inspection, placed on the filter; and discharges the sucked solution and materials.

In order to achieve the objectives of the present invention, in a state where the slide is located on the upper end of the filter on which the examination objects are placed, when the blower unit firstly blows air to the filter, a collecting film of the filter swells and approaches the slide so that the examination objects are placed on the slide; and when the blower unit secondly blows air to the filter, the examination objects are uniformly spread on and simultaneously firmly placed onto the slide.

In order to achieve the objectives of the present invention, the examination object placing apparatus further includes a ratio turbidity measurement means for measuring turbidity of the mixed solution to determine the distribution ratio of the examination objects contained in the mixed solution of the container.

In order to achieve the objectives of the present invention, the examination object placing apparatus further includes a barcode recognition means for checking whether the barcodes attached to the container and the slide match with each other.

Figure 1:
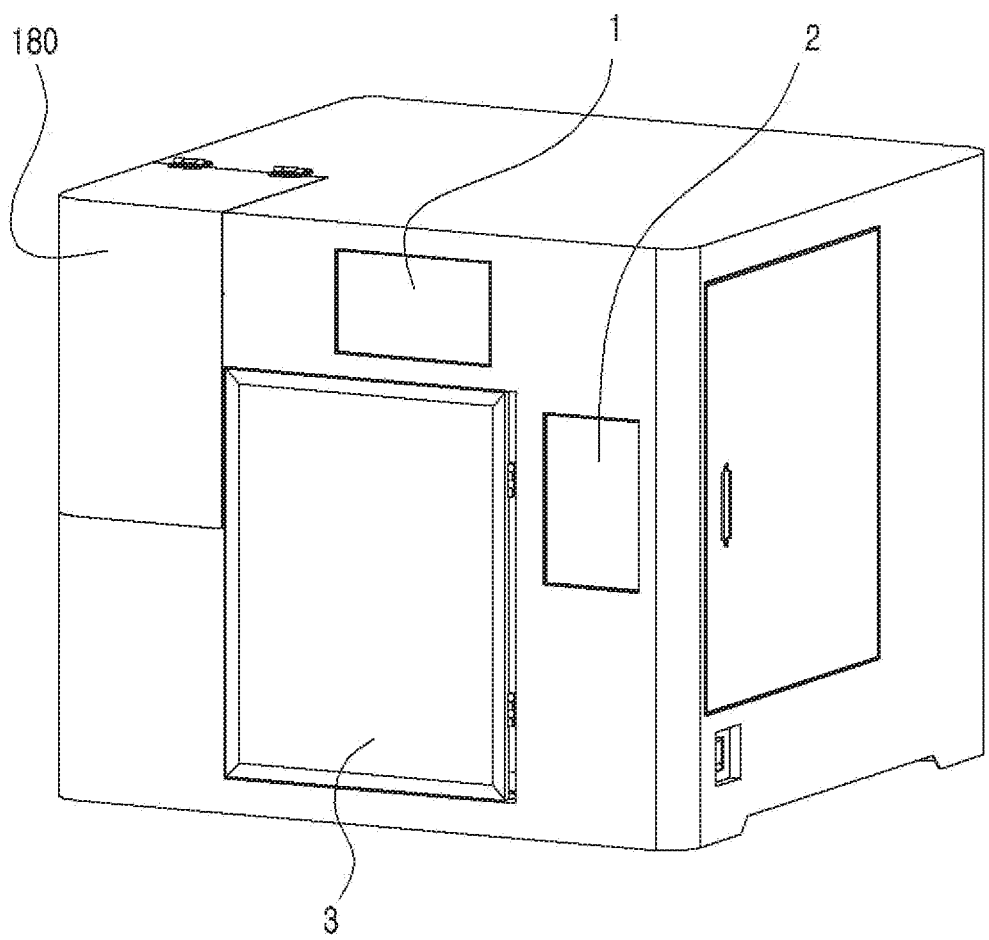
FIG. 1 is a perspective view showing the appearance of the apparatus for placing objects to be examined by blowing, according to an embodiment of the present invention.

| <Brief description of symbols in the drawings> | |
|---|---|
| 10: container | 11: first cap filter |
| 20: slide | 50: filter |
| 51: porous insert | 52: support |
| 52a: through-hole | 54: coupling flange |
| 58: circumferential coupling groove | |
| 110: container fixing means | |
| 120: cap opening-closing means | |
| 130: filter transfer rail | |
| 140: suction unit | 141: flange |
| 142: inner space | 150: blower unit |
| 151: flange | 152: inner space |
| 153: nozzle | 160: slide fixing means |

DETAILED DESCRIPTION OF EMBODIMENTS

Hereinafter, embodiments of the present invention are described in detail with reference to the accompanying drawings. Descriptions of well-known parts of the configurations may be omitted or provided briefly to avoid obscuring the subject matter of the invention; however, it will be appreciated to those skilled in the art that they are used for the present invention.

Figure 2:
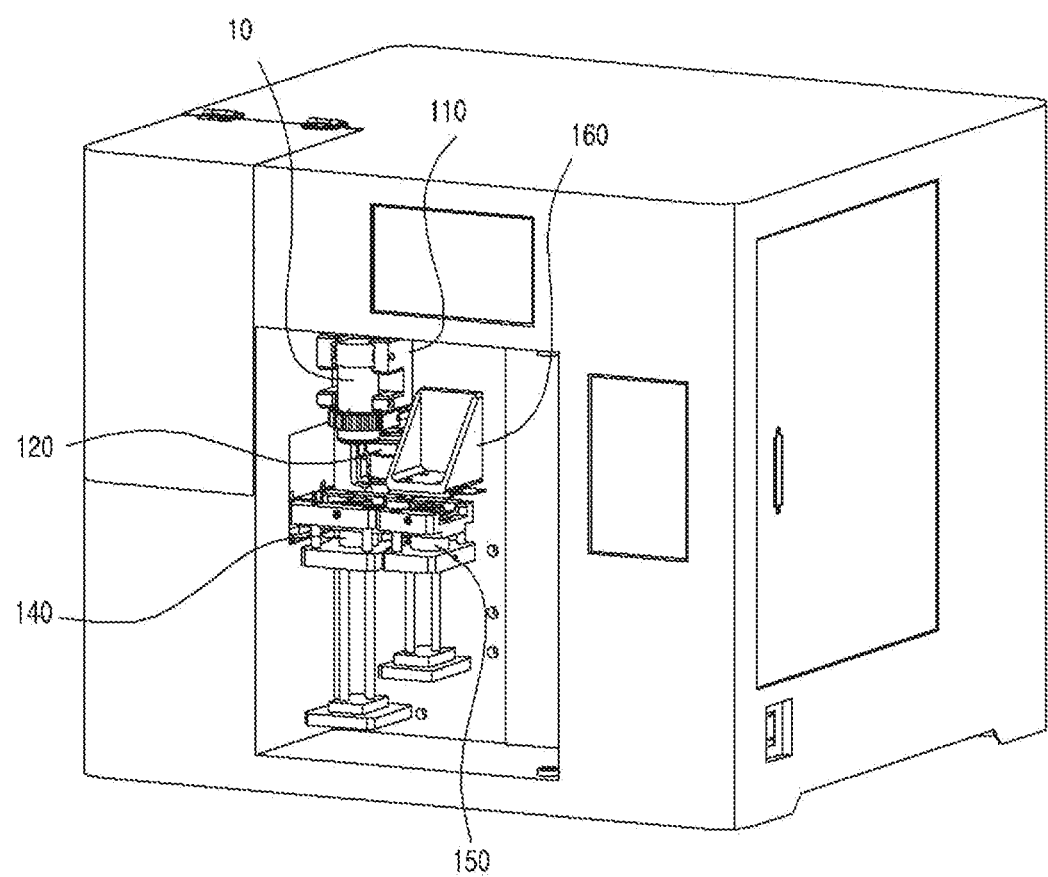
FIG. 2 is a perspective view of the apparatus of FIG. 1, removing the front door.
Figure 3:
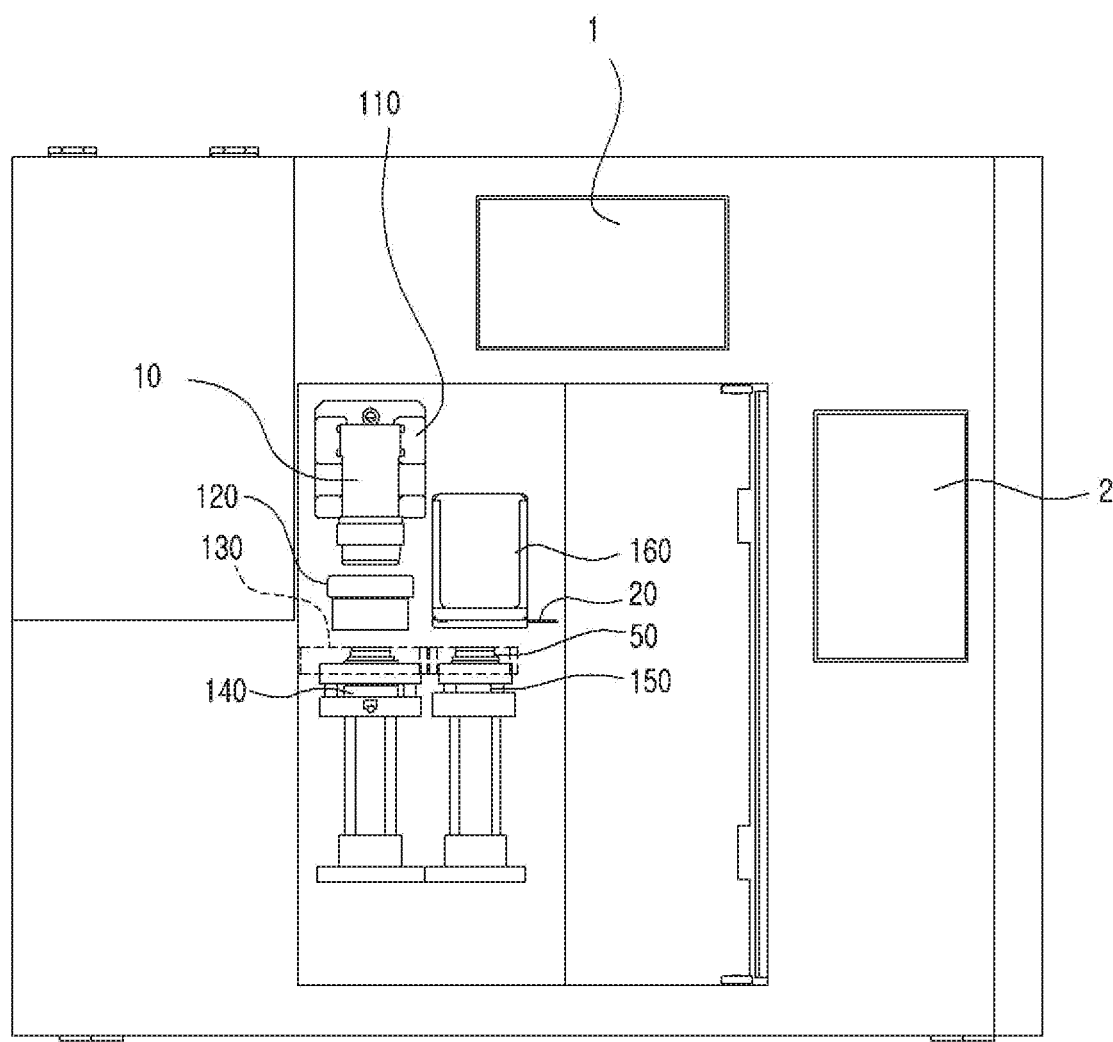
FIG. 3 is a front view of FIG. 2.
Figure 4:
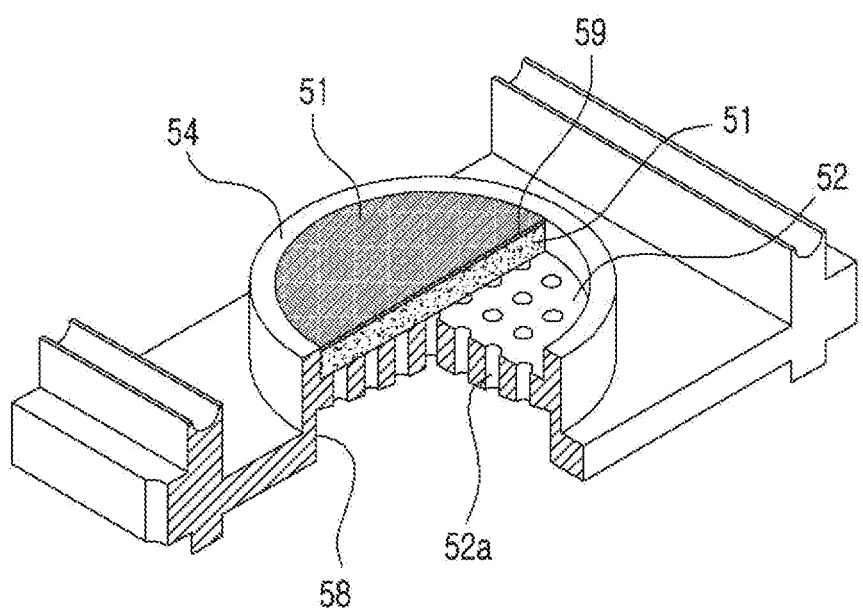
FIG. 4 is a partially perspective view of the filter used in the apparatus for placing objects to be examined by blowing, according to an embodiment of the present invention.

FIG. 1 is a perspective view showing the appearance of the apparatus for placing objects to be examined by blowing, according to an embodiment of the present invention; FIG. 2 is a perspective view of the apparatus of FIG. 1, removing the front door; FIG. 3 is a front view of FIG. 2; and FIG. 4 is a partially perspective view of the filter used in the apparatus for placing objects to be examined by blowing, according to an embodiment of the present invention.

As shown in FIGS. 1 to 4, an apparatus for placing objects to be examined (hereafter called an examination object placing apparatus) 100 according to an embodiment of the present invention includes a container fixing means 110, a cap opening-closing means 120, a filter transfer means (not shown), a suction unit 140, a blower unit 150 and a slide fixing means 160.

The container fixing means 110 is provided to hold a container 10 that containing a mixed solution with examination objects such as cells. The mixed solution contained in the container 10 is formed as examination objects are mixed with a solution. The container fixing means 110: is located above of the suction unit 140 that will be described below; supports the container 10 so that the opening of the container faces down; and raises or lowers the container 10.

The container 10, used in the examination object placing apparatus 100 according to an embodiment, is configured to include a first cap filter 11 at the opening. The first cap filter 11 is formed with small holes for preventing the mixed solution from being quickly poured out of the opening of the container 10 and filtering materials such as MUCUS disturbing the inspection. When the suction unit 140 is operated, the mixed solution in the container 10 flows out of the container 10 through the first cap filter 11.

The cap opening-closing means 120 is provided to open or close the cap of the container 10 and is located below the container 10 fixed to the container fixing means 110. The cap opening-closing means 120: is formed to move back and forth and is located below the container fixing means 110;

holds and turns the cap of the container 10 in a direction to open it; and moves back to original position so as not to disturb the attachment of the filter to the opened opening of the container 10.

The filter transfer means (not shown) is provided to transfer the filter 50 onto the suction unit 140 and the blower unit 150 along the filter transfer rail 130. The filter transfer means (not shown) is equipped with a transfer bar (not shown) coming cut/off in the width direction in order to push the filter 50, located at the left of the suction unit 140, to the suction unit 14 or the blower unit 150, where the transfer bar pushes the filter 50 to the right and then moves back to the original position.

The filter 50 is stacked and stored in the filter storing unit 180 located at the left of the suction unit 140.

As shown in FIG. 4, the filter 50 is configured in such a way that: a collecting film 59, which is transparent and has small holes of a laminate structure on the upper side, supported by a porous insert 51; a support 52, having a number of through holes 52a, is formed under the porous insert 51; and a coupling flange 54 is formed around the support 52, where the coupling flange 54 is circumferentially protruded in the upper direction and can be inserted into the opening of the container 10 containing a mixed solution with objects.

The filter 50 forms a circumferential coupling groove 58 on the lower side of the filter 50, corresponding to the opposite side on which the coupling flange 54 is formed, where the circumferential coupling groove 58 is fitted into a protruded flange 141 circumferentially protruded from the suction unit 140 which will be described later.

Figure 5:
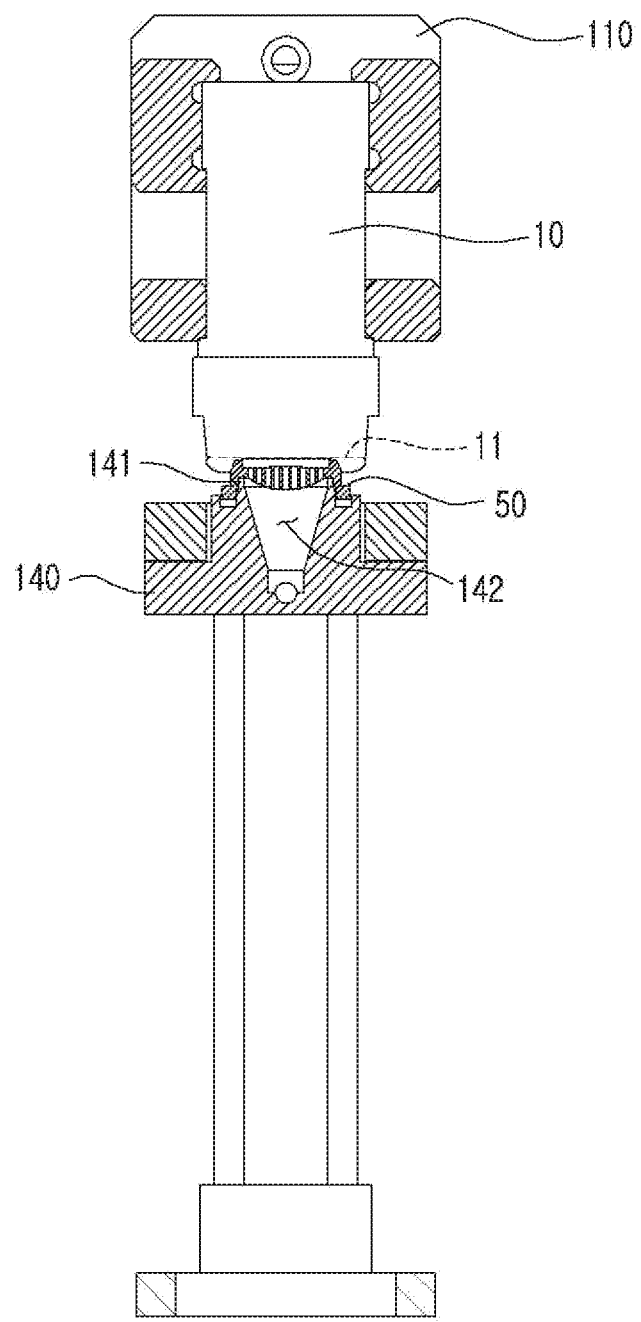
FIG. 5 is a front view showing a state where the filter is coupled to the opening of the container in the apparatus for placing objects to be examined by blowing, according to an embodiment of the present invention.
Figure 6:
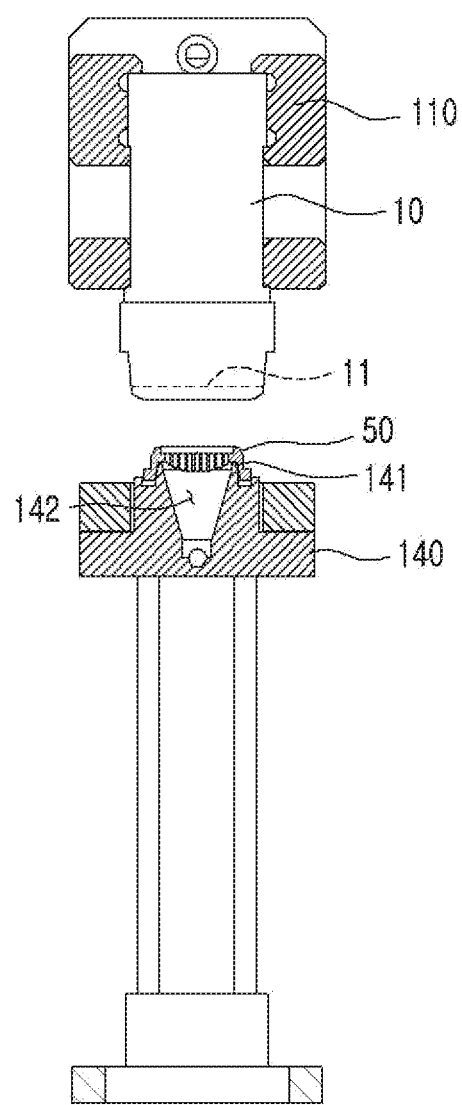
FIG. 6 is a front view showing a state where the filter is separated from the container in the apparatus for placing objects to be examined by blowing, according to an embodiment of the present invention.
Figure 7:
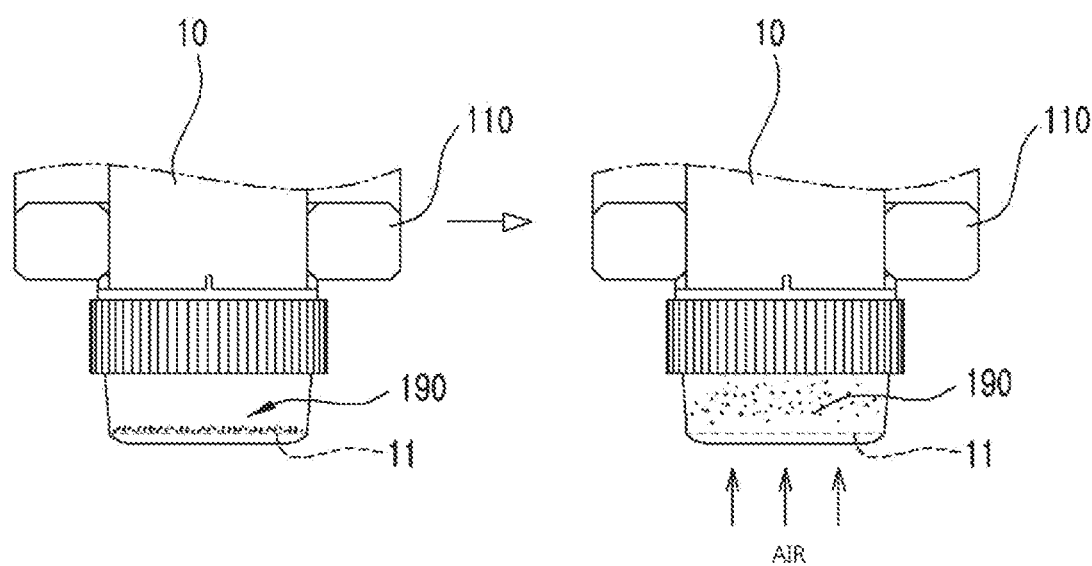
FIG. 7 is a conception diagram showing a state where objects to be examined are floated in the container as the suction unit blows air, in the apparatus for placing an objects to be examined by blowing, according to an embodiment of the present invention.

FIG. 5 is a front view showing a state where the filter is coupled to the opening of the container in the apparatus for placing objects to be examined by blowing, according to an embodiment of the present invention. FIG. 6 is a front view showing a state where the filter is separated from the container in the apparatus for placing objects to be examined by blowing, according to an embodiment of the present invention. FIG. 7 is a conception diagram showing a state where objects to be examined are floated in the container as the suction unit blows air, in the apparatus for placing objects to be examined by blowing, according to an embodiment of the present invention.

Referring to FIGS. 3, 5 and 6, the suction unit 140 is provided to place the examination objects on the filter 50. The suction unit 140 forms a circumferentially protruded flange 141 on the upper end. Then as the suction unit 140 moves up, the flange 141 is placed into the circumferential coupling groove 58 of the lower end of the filter 50. The flange 141 forms an inner space 142 in the inside to form negative pressure. The inner space 142 communicates an air ejecting and sucking means (not shown). The air ejecting and sucking means is implemented with a pump for ejecting and sucking air. When the filter 50 is placed on the suction unit 140, the suction unit 140 vertically moves up so that a coupling flange 54 of the filter, protruded in the upper direction, is tightly attached to the opening of the container 10, as shown in FIG. 5.

When the filter 50, located at the upper portion of the suction unit 140, is tightly attached to the opening of the container 10 containing a mixed solution, the air ejecting and sucking means (not shown) expels air to the filter 50, which is called a blowing process, as shown in FIGS. 5 and 7. That is, when the suction unit 140 expels air to the filter 50, the air flows into the container 10 via the filter 50 through the opening of the container 10, so the examination objects, settled to the first cap filter 11 of the container 10, are floated and uniformly spread in the mixed solution in the container 10.

When the blowing process is terminated, the air ejecting and sucking means of suction unit 140 sucks air in the inner space 142 of the flange 141, creating negative pressure in the inner space 142, so that the mixed solution comes down out of the container 10, flowing through the first cap filter 11 of the container 10. When the mixed solution flows through the first cap filter 11 of the container 10, it passes through the collecting film 59, the porous insert 51 and the through-holes 52a of the support 52 of the filter 50 and is sucked into the suction unit 140, and the examination objects remain on the collecting film 59 because they do not pass through the collecting film 59.

Meanwhile the suction unit 140 may be configured in such a way as to detect pressure in the inside through the pressure sensor (not shown) of the inside, and to control the process of placing examination objects on the filter 50. That is, when the air ejecting and sucking means of the suction unit 140 sucks air from the inner space 142, the examination objects are piled on the collecting film 59 of the filter 50 and blocks the small holes of the collecting film 59. In that case, the inner space of the suction unit 140 gradually decreases in pressure. Therefore, when the pressure detected by the pressure sensor of the suction unit 140 reaches a preset value of pressure, the air ejecting and sucking means stops sucking air.

When the pressure detected by the pressure sensor of the suction unit 140 reaches a preset value of pressure, it means that a required amount of the examination object has been placed on the collecting film 59 of the filter 50. The preset value of pressure, as a threshold for the suction interruption, may vary according to types of objects and may be set and reset.

The air ejecting and sucking means of the suction unit 140 may repeat the suction process one or more times in a state where the filter 50 and the container 10 are tightly attached to each other. That is, performing and releasing the suction are alternatively repeated in order to increase the amount of examination objects gathering on the collecting film 59 of the filter 50, and these processes are useful when the amount of mixed solution remaining in the container 10 is relatively small. That is, when a relatively small amount of mixed solution remains in the container 10, a required amount of examination objects may not be gathered on the collecting film 59 by generating negative pressure only once. Therefore, as the suction means repeats the performing and releasing processes of suction, tension and relaxation are repeatedly generated in the filter 50 and the first cap filter 11, so that, although a relatively small amount of mixed solution remains in the container 10, the largest possible remaining amount of examination objects can be gathered on the collecting film 59. The repetition number of suction by the air ejecting and sucking means may be set or reset.

When the examination objects in mixed solution contained in the container 10 are placed on the filter 50 by the suction unit 140, the container fixing means 110 moves the container 10 up and thus the filter 50 is separated from the opening of the container 10.

Figure 8:
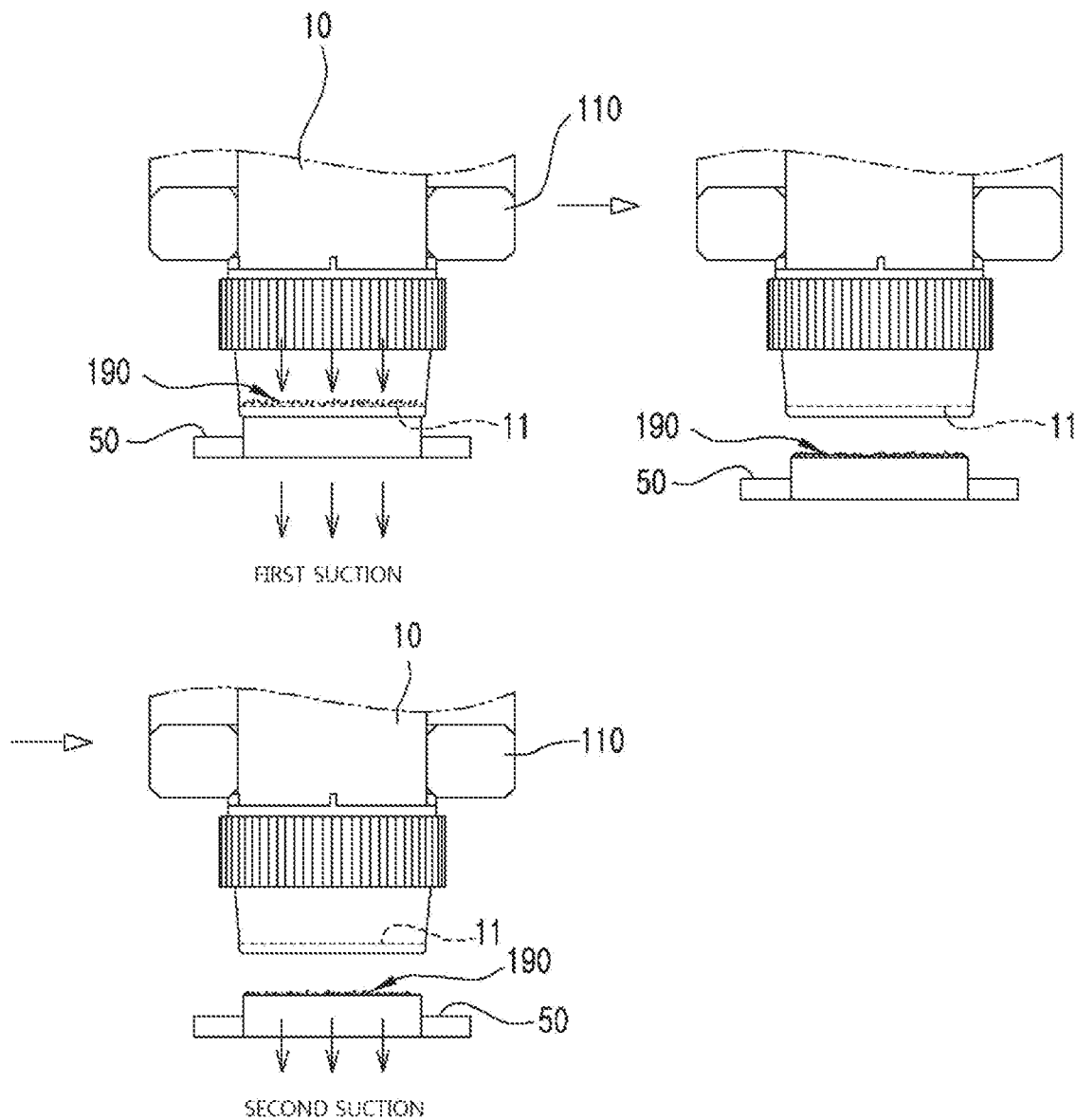
FIG. 8 is a concept diagram describes how a suction unit of the apparatus for placing objects to be examined by blowing, according to an embodiment of the present invention, performs the first suction of a mixed solution from a container and then the second suction of a filter in a state where the container and the filter are separated from each other.

FIG. 8 is a concept diagram describes how a suction unit of the apparatus for placing objects to be examined by blowing, according to an embodiment of the present invention, performs the first suction of a mixed solution from a container and then the second suction of a filter in a state where the container and the filter are separated from each other.

As shown in FIGS. 6 and 8, in a state where the filter 50 is separated from the opening of the container 10, the suction unit 140 additionally re-performs a suction process with a proper level of suction force (or a proper amount of suction). When the suction unit 140 additionally performs a suction process in a state where the filter 50 is separated from the container 10, it sucks a solution and materials hindering the inspection, except for the examination objects remaining on the collecting film 59 of the filter 50, so that only the examination objects and a small amount of liquid required for the inspection are left on the collecting film 59 of the filter 50. If the suction unit 140 sucks the mixed solution from the container 10 and moves the filter 50 with the collecting film 59 on which the mixed solution is placed and applies a placing process to the slide it is difficult to place the slide with pure examination objects due to the solution and materials hindering the inspection. When an excessive amount of solution exists on the collecting film 59 of the filter 50, the solution is widely spread over the attachment area on the slide 20 to which the examination objects are attached during the attachment of examination objects on the slide 20. Therefore, the examination objects are distributed over a useless area out of observation; and the examination objects are not well transferred from the filter 50 to the slide 20 by air ejection; and the ratio of attachment of examination objects to the slide 20 is, when the examination objects are transferred, decreased because of the solution.

When completing the additional suction process, the suction unit 140 moves down and is thus separated from the filter 50. The filter transfer means (not shown) transfers the filter 50 with the examination objects to the lower side of the slide fixing means 160 and simultaneously the upper side of the blower unit 150.

The slide fixing means 160 located at the upper end of the blower unit 150 is opened downward and supports the slide 20 so that the placement surface of the slide 20 is exposed down.

Figure 9:
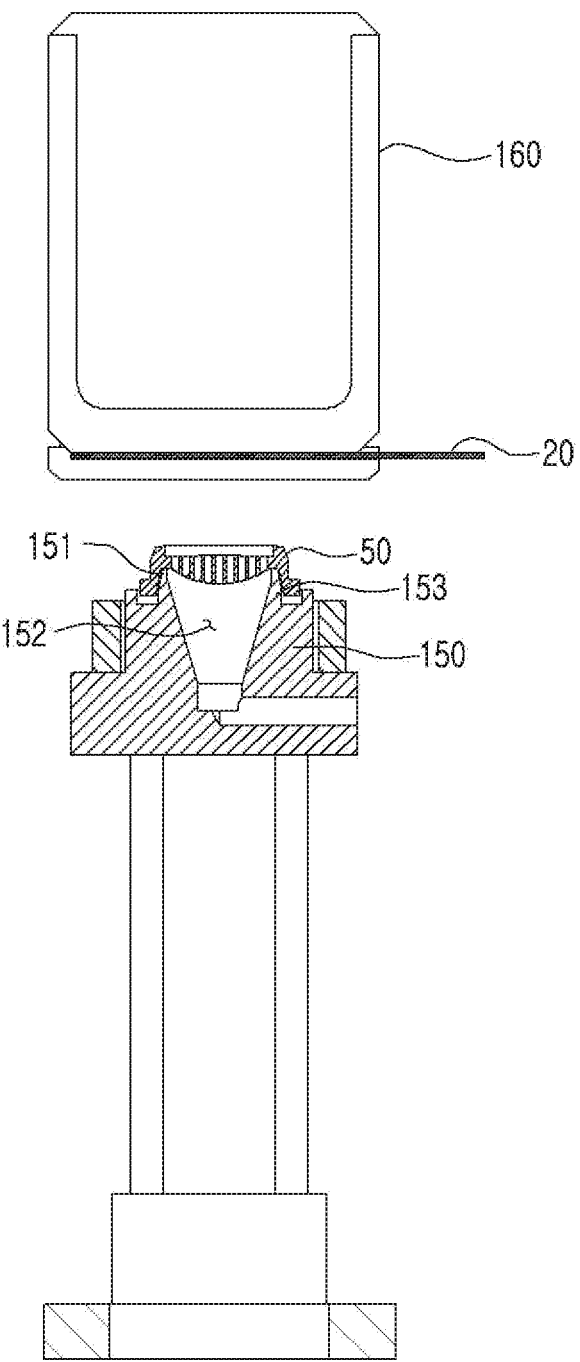
FIG. 9 is a front view showing the apparatus for placing objects to be examined by blowing, according an embodiment of the present invention, when the filter is moved to the blower unit.
Figure 10:
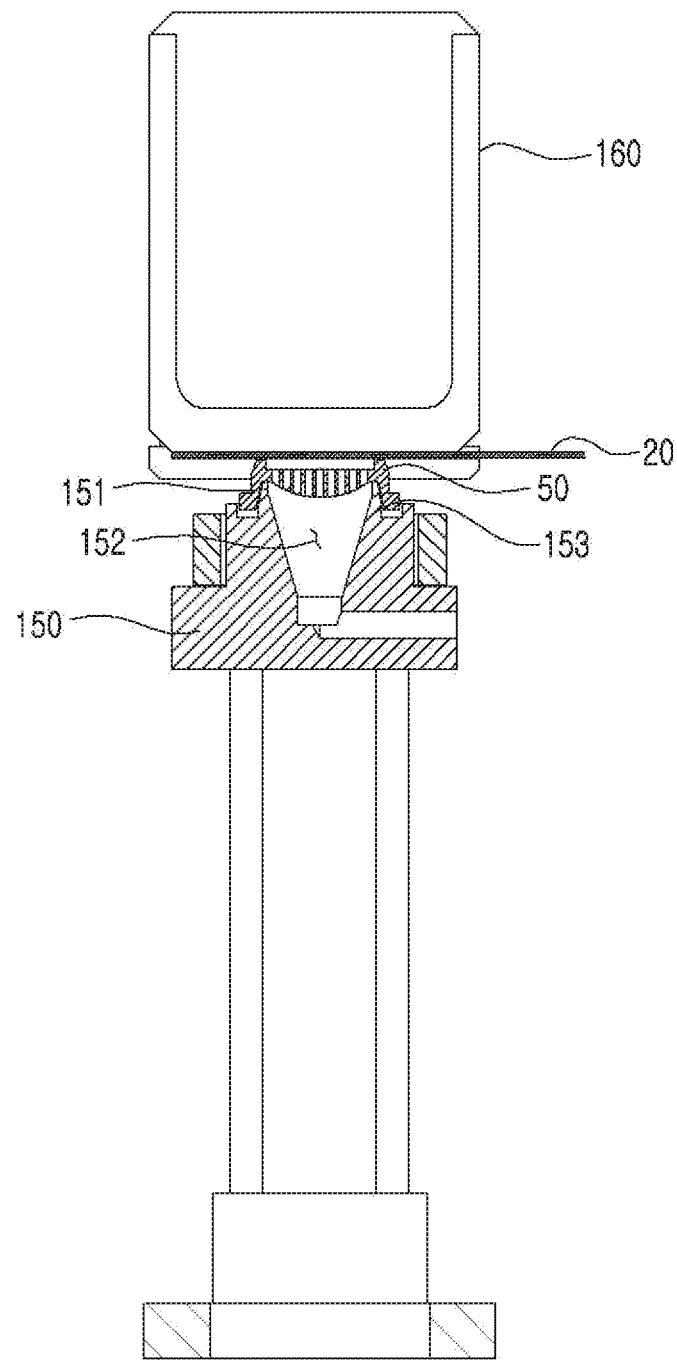
FIG. 10 is a front view showing the apparatus for placing objects to be examined by blowing, according an embodiment of the present invention, when the blower unit moves up and the filter is close to the placement surface of the slide.
Figure 11:
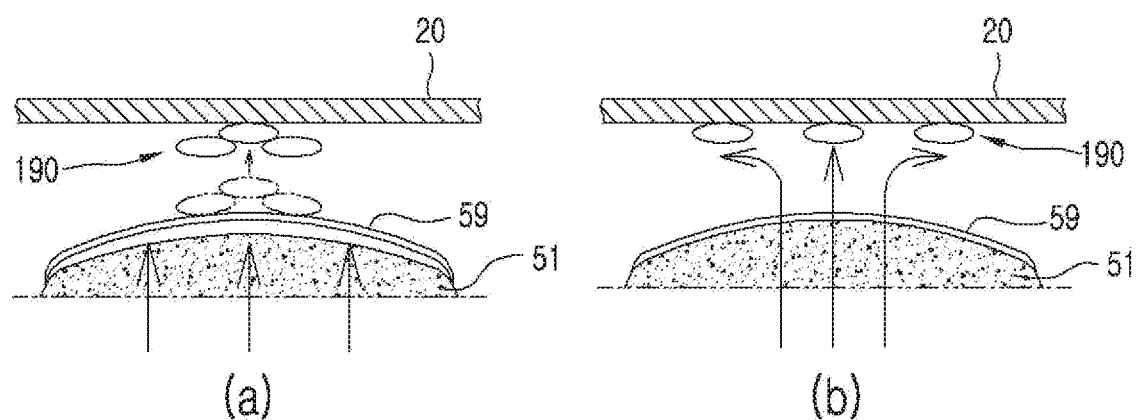
FIG. 11 shows a concept diagram (a) of states where examination objects on the filter are placed on the slide in the first blowing process performed by a blower unit of the apparatus for placing objects to be examined by blowing according an embodiment of the present invention; and a concept diagram (b) of states where the examination objects are uniformly spread on and firmly placed on the slide in the second blowing process performed by the blower unit.

FIG. 9 is a front view showing the apparatus for placing objects to be examined by blowing, according an embodiment of the present invention, when the filter is moved to the flower unit. FIG. 10 is a front view showing the apparatus for placing objects to be examined by blowing, according an embodiment of the present invention, when the blower unit moves up and the filter is close to the placement surface of the slide. FIG. 11 shows a concept diagram (a) of states where examination objects on the filter are placed on the slide in the first blowing process performed by a blower unit of the apparatus for placing objects to be examined by blowing according an embodiment of the present invention; and a concept diagram (b) of states where the examination objects are uniformly spread on and firmly placed on the slide in the second blowing process performed by the blower unit.

As shown in FIGS. 3, 9 and 10, the blower unit 150 is provided to eject air to the filter 50 to transfer the examination objects placed on the filter 50 to the slide 20. The blower unit 150 forms a circumferentially protruded flange 151 at the upper end and is equipped with a space 152 for generating positive pressure in the inside of the flange 151.

When the filter 50 is transferred to the upper part of the blower unit 150 and then the blower unit 150 moves up, the circumferentially protruded flange 151 of the upper end of the blower unit 150 is coupled to the circumferentially coupling groove 58 of the lower end of the filter 50. As such, the blower unit 150 is vertically moved up to place the filter 50 on the top and then moves up with the filter 50, so that the collecting film 59 on the upper part of the filter 50 is close to the placement surface of the slide 20. After that, the blower unit 150 performs the first ejection of air to the lower side of the filter 50. When the air is ejected to the filter 50, the collecting film 59 of the filter 50 swells upward; a dielectric polarization phenomenon simultaneously occurs between the collecting film 59 and the placement surface of the slide 20; the examination objects are transferred, without deformation, as a single layer, to the placement surface of the slide 20 and then attached to the surface (as shown in FIG. 11(a)).

After completing the first air ejection, the collecting film 59 remains without any operation for a certain period of time. In that case, the collecting film 59 is tightly attached to the porous insert 51. After that, the second ejection of air is performed. The second air ejection is a process to re-expel air to the examination objects placed on the placement surface of the slide 20. The second air ejection is to uniformly spread the placed examination objects on the slide 20 without making a lump and, simultaneously, to firmly attach the examination objects onto the slide 20 (as shown in FIG. 11 (b)).

As such, the examination objects located on the collecting film 59 of the filter 50 are placed on the placement surface of the slide 20 by the air ejection of the blower unit 150.

The ejection amount of air and the ejection number of air from the nozzle 153 of the blower unit 150 may be pre-set according to types of examination objects.

As such, since the examination objects are placed on the placement surface of the slide 20 by the blower unit 150 in a state where the filter 50 and the placement surface of the slide 20 are minutely spaced apart from each other, damage of examination objects, such damage caused by pressing the examination objects, can be prevented as much as possible, and instead the examination objects can be uniformly distributed and attached onto the placement surface of the slide 20 by air pressure.

When the examination objects, placed on the collecting film 59 of the filter 50, are transferred and placed onto the placement surface of the slide 20 by the blower unit 150, the blower unit 150 moves down back to the original position and the filter 50 on the blower unit 150 is, for the following process, pushed by a new filter 50 transferred by the filter transfer means (not shown) and falls down in the filter collecting box (not shown).

Meanwhile, the suction unit 140 and the blower unit 150 each includes at the lower end: a means for vertically transferring the suction unit 140 and the blower unit 150; a means for sucking or discharging air through the nozzle 153 of the blower unit 150 and the air ejecting and sucking means (not shown) of the suction unit 140, in other word a means for controlling air pressure; and a means for collecting liquid dropped into the inner space 142 of the suction unit 140. The means for vertically moving the suction unit 140 and the blower unit 150 may be implemented with various types of means, such as an air pressure cylinder, a liquid pressure cylinder, a lead screw, etc.

Meanwhile, the examination object placing apparatus 100 according to an embodiment of the present invention includes touch-screen based display means 1 and 2 and a control means (not shown).

The control means controls the respective components according to instructions input to the display means 1 and 2.

In addition, the control means stores numerals and instructions coded for controlling the respective components through a program. According to instructions input to a display means 220, the programmed content and a measurement by a pressure sensor, the control means: controls a filter transfer means (not shown); controls a cap opening-closing means 120; transfers the suction unit 140; controls the air ejection amount, the air suction amount, the number of air ejections, and the number of air suctions by the air ejecting and sucking means (not shown); transfers the blower unit 150; controls the amount of air discharge and the number of air collections through the nozzle; etc. The control means may transmit various working states to the display means 220, so that the user can view the working states through the display means 220.

In the following description, a process is explained that places examination objects on a slide by using an apparatus for placing object to be examined by using blowing, according to the present invention.

The container 10, containing a mixed solution with examination objects, such as cells, is fixed, with the opening facing down, to a container fixing means 110.

The cap opening-closing means 120 moves forward to the below of the container 10 fixed to the cap fixing means 110, holds and turns the cap of the container 10 in a direction to open the cap from the container 10, and then moves back in the rear direction.

The filter transfer means (not shown) transfers the filter 50 to the suction unit 140.

As the suction unit 140 moves up, the flange 141 of the suction unit 140 is coupled to the circumferentially coupling groove 58 of the lower end of the filter 50. When the filter 50 is coupled to the suction unit 140, the suction unit 140 is vertically moved up and thus the coupling flange 54, protruded in the upper direction along the filter 50, is tightly closed to the opening of the container 10.

When the filter 50 is tightly closed to the opening of the container 10, the suction unit 140 expels air through the filter 50 to the inside of the container 10, so that examination objects 190 settled in the first cap filter 11 of the container 10 are floated and thus uniformly spread in the mixed solution.

That is, since the container 10 is fixed, with the opening facing down, to the container fixing means 110, the examination objects inside the container 10 are settled down in the bottom of the first cap filter 11 of the container 10. Therefore, since the first cap filter 11 of the container 10 has examination objects with a relatively high level of density, a relatively large amount of examination objects is discharged to the filter 50 by the first suction of the suction unit 140 and then a relatively small amount of examination objects is discharged to the filter 50 by the second suction. That is, initially the examination objects are excessively and densely gathered in the first cap filter 11 of the container 10, so that the first suction process discharges a relatively large amount of examination objects, and the following suction processes discharges the remarkably decreased amount of examination objects. As such, in order to prevent a large deviation in the amount of examination objects from being generated each time the suction is performed, the present invention performs a blowing process so that the examination objects settled in the first cap filter 11 are uniformly spread over the entire area of the mixed solution as shown in FIG. 7, before the suction unit 140 performs a suction process. Therefore, when a number of suctions are performed to suck the mixed solution from the container 10, the same amount of examination objects to be placed on the filter 50, forming the same distribution ratio, is sucked each time the suction is performed, thereby ensuring the sameness of the examination objects in extraction.

When the blowing process by the suction unit 140 is terminated, the air ejecting and sucking means (not shown) of the suction unit 140 sucks the air from the inner space of the flange 141, so that the mixed solution flows down out from the container 10, passing through the first cap filter 11 of the container 10.

The examination objects flowing down out of the container 10 are placed on the collecting film 59 of the filter 50.

When the inner pressure of the suction unit 140 reaches a preset value of pressure, the suction process by the suction unit 140 is stopped, and then the suction unit 140 moves down, so that the filter 50 is separated from the opening of the container 10.

In a state where the filter 50 is separated from the opening of the container 10, the suction unit 140 additionally re-performs a suction process with a proper level of suction force (or a proper amount of suction) to additionally suck and discharges a solution and materials hindering the inspection remaining on the collecting film 59 of the filter 50, so that only the examination objects and a small amount of liquid required for the inspection are left on the collecting film 59 of the filter 50 as shown in FIG. 8.

When completing the additional suction process, the suction unit 140 moves down and is thus separated from the filter 50. The filter transfer means (not shown) transfers the filter 50 to a space between the slide 20 and the blower unit 150.

After that, the blower unit 150 is vertically moved up so that the filter 50 is coupled to the upper end of the blower unit 150, and then moves up with the filter 50, so that the collecting film 59 of the filter 50 is close to the placement surface of the slide 20. As shown in FIGS. 10 and 11, the blower unit 150 performs the first ejection of air to the lower side of the filter 50, so that the collecting film 59 of the filter 50 swells upward, and simultaneously this causes an instantaneous dielectric polarization phenomenon, so that the examination objects are transferred, without deformation, as a single layer, to the placement surface of the slide 20 and then attached to the surface of the slide 20.

After a period of time for pause has elapsed from time that the first air ejection process is terminated, the blower unit 150 re-performs the second ejection of air. The second air ejection by the blower unit 150 allows the examination objects 190 placed on the placement surface of the slide 20 to be uniformly spread on the slide 20 without creating any lumps and to be firmly attached onto the slide 20.

When the examination objects from the filter 50 have been placed onto the placement surface of the slide 20 by the blower unit 150, the blower unit 150 moves down and is separated from the filter 50, and the filter 50 is pushed by a new filter 50 transferred by the filter transfer means (not shown) and falls down in the filter collecting box.

As described in detail above, since the apparatus according to the present invention performs a blowing process before the suction unit 140 performs a suction process, the examination objects settled in the first cap filter 11 of the container 10 are floated and uniformly spread in the entire area of the mixed solution, thereby ensuring the sameness of the examination objects extracted by every suction.

The examination object placing apparatus of the present invention includes a container storing examination objects. The container is equipped with the first cap filter. Since the container is installed so that the opening faces down, the examination objects are unavoidably settled in the first cap filter. When a suction process is performed in a state where the examination objects are settled in the first cap filter, a relatively large amount of examination objects is sucked, compared with the suction amount of mixed solution. When the filter is replaced with a new filter and the suction process by the suction unit is performed a certain number of times in the way described above, although the same amount of mixed solution is sucked, the amount of sucked examination objects continues to decrease each time the suction is performed. That is, a problem exists where the first suction process sucks an excessively large amount of examination objects to be placed on the slide and the following suction processes acquire decreased amount of examination objects each time that the suction process is repeated. That is, the problem is that the sameness of the acquired amount of examination objects is not guaranteed.

The present invention resolves the problems described above.

When the suction unit of the present invention places examination objects from the container to the filter, the suction unit firstly performs a blowing process for expelling air to the filter, so that the examination objects, settled in the first cap filter of the container, are floated in the mixed solution and thus uniformly spread in the mixed solution. In a state where the examination objects are uniformly spread in the mixed solution, the suction unit secondly sucks the mixed solution, thereby placing the examination objects on the filter. Therefore, each time that the suction unit performs a suction process, a uniform amount of examination objects is placed on the filter, which is a remarkable advantage.

In addition, when the suction unit 140 sucks a mixed solution and performs the placement process to the filter 50, the suction unit 140 performs an additional suction process in a state where the container 10 and the filter 50 are separated from each other, so that a solution and materials hindering the inspection, remaining on the filter 50, are removed from the filter 50. Therefore, the examination objects can be placed at the precise location on the slide 20 with a high level of yield. In addition, the purity of the examination objects placed on the slide can be increased.

In addition, by using a pressure sensor, only a certain amount of objects may be placed on the filter 50 and then placed on the slide 20.

Since objects can be spread uniformly, without overlapping, on the slide 20, by air pressure, the accuracy of inspection can be improved.

In addition, since objects can be placed on the slide 20 by air pressure, no physical contact is made with the objects, so that the objects are not damaged.

Although a small amount of the objects are contained in the mixed solution, almost the entire amount of the objects remaining in the container may be placed on the filter by repeating the generating of negative pressure a number of times. Since the objects are placed on the slide 20 by instantaneous air pressure, which differs from conventional methods, the velocity of movement is remarkably increased and most of the examination objects placed on the filter 50 are transferred to the slide 20. Since most of the examination objects placed on the filter 50 are transferred to the slide 20, the remaining amount of examination objects on the filter 50 is very small. Therefore, the efficiency of transferring objects from the filter 50 to the slide 20 is improved.

According to the present invention, cells from the container 10 containing a mixed solution where a solution is mixed with objects, such as cells, etc., are separated from the container 10 and collected on the slide 20, which is performed through automated processes. Therefore, the process time is shortened and there is no concern regarding the transfer of contaminants or impurities from the user's hands to the slide 20.

In addition, the examination object placing apparatus according to the present invention may be equipped with a ratio turbidity measurement means (not shown) that measures the amount of examination objects, such as cells, in a container in which a mixed solution is contained. The ratio turbidity measurement means, installed in the vicinity of the container fixing means, measures the turbidity of the mixed solution contained in the container and determines whether the distribution ratio of the examination objects in the mixed solution is high or low. When the level of turbidity measured by the ratio turbidity measurement means is high, the examination object placing apparatus ascertains that a relative large amount of examination objects is contained in the mixed solution. When the level of turbidity measured by the ratio turbidity measurement means is low, the examination object placing apparatus ascertains that a relative small amount of examination objects is contained in the mixed solution. When the examination object placing apparatus ascertains that the level of turbidity measured by the ratio turbidity measurement means is high and thus that a relative large amount of examination objects is contained in the mixed solution, a sufficient amount of examination objects can be placed on the filter although the strength of suction by the suction unit is low. Therefore, the control means sets the suction strength of the suction unit to be low. When the level of turbidity measured by the ratio turbidity measurement means is low, the control means sets the suction strength of the suction unit to be high. Accordingly, although the level of turbidity varies, a proper amount of cells to be examined can be extracted from the container and the cells to be examined can be placed, with a single layer, on the filter and the slide. The ratio turbidity measurement means (or transparency measurement, means) may be implemented with various types of instruments which are well-known, and thus the detailed description will be omitted.

In addition, the examination object placing apparatus according to the present invention may be equipped with a barcode recognition means (not shown). In this case the mixed solution container and the slide have barcodes recording information. The barcode recognition means reads the barcodes from the mixed solution container and the slide respectively and compares them with each other to check whether they are matched with each other. Therefore, although the examination object placing apparatus simultaneously processes a varied amount of examination objects, the barcode recognition means can prevent respective examination objects from being mixed, thereby securing the reliability of inspection. The barcode recognition means may be implemented with various types of means which are well-known, and thus the detailed description will be omitted. The barcode recognition means may be installed to a proper location, such as the vicinity of slide fixing means and the container fixing means, in order to read the barcodes attached to the slide and the container.

The present invention has the following advantages.

First, since the present invention blows the air to the mixed solution containing samples stored in the container, it can uniformly spread the samples in the mixed solution of the container and thus ensure the sameness of the objects to be extracted.

When the present invention sucks a mixed solution from a container through a filter in order to extract samples, it separates the filter from the container and performs an additional suction process, irrespective of the suction process for extraction; additionally removes the materials hindering the inspection and the extracted excessive solution on the filter; and thus places the extracted samples on the slide with a relatively high degree of purity.

In addition, since the present invention displays, in real-time, the control and operation processes of the apparatus on the display, the user can easily operate the apparatus, while viewing the current operation states in real-time.

Although embodiments of the invention have been described in detail above, it should be understood that many variations and modifications of the basic inventive concept herein described, which may be apparent, to those skilled in the art, will still fall within the spirit and scope of the embodiments of the invention as defined in the appended claims.

What is claimed is:

1. An apparatus for handling examination objects, the apparatus comprising:
   a container holder;
   a suction unit positioned to be fluidically coupled to a container held by the container holder;
   a blower;
   a filter transfer device movable to transfer a filter from the suction unit to the blower; and
   a controller in communication with the suction unit and the blower, wherein the controller is programmed to cause the apparatus to perform operations including:
      prior to drawing a solution from the container and through the filter, outputting air from the suction unit such that the air flows upwardly through a lower side of a cap filter of the container to cause examination objects resting on an upper side of the cap filter to be uniformly spread in the solution held in the container; and
      after uniformly spreading the examination objects in the solution,
         sucking, using the suction unit, the solution through the cap filter to cause the examination objects to be collected along a collection surface of the filter,
         robotically move the filter, which carries the examination objects, away from the container,
         after robotically moving the filter away from the container, causing the suction, unit to suck solution from the filter,
         robotically moving, using the filter transfer device, the filter from the suction unit to the blower while the filter carries the examination objects located along the collection surface, and
         blowing, using the blower, the examination objects from the collection surface onto a surface of a slide.

2. The apparatus of claim 1, wherein the controller is programmed to determine whether a predetermined amount of examination objects has been collected on the collection surface prior to transferring the examination objects to the surface of the slide.

3. The apparatus of claim 1, wherein the controller is programmed to cause the blower to blow a sufficient amount of air through the filter to cause a collection film of the filter to bulge toward the slide to promote transfer of the examination objects from the collection surface to the surface of the slide.

4. The apparatus of claim 1, wherein the blower is configured to output air toward the filter to cause a region of a collection film to displace toward the slide to promote transfer of the examination objects from the region to the surface of the slide.

5. The apparatus of claim 1, wherein the controller is further programmed cause the blower to output air that causes a region of the collection film carrying the examination objects to become spaced apart from a filter body of the filter.

6. The apparatus of claim 1, further comprising one or more touch-screen displays in communication with the controller, wherein the controller stores coded instructions for controlling the suction unit and the blower.

7. An apparatus for handling examination objects, the apparatus comprising:
   a container holder;
   a suction unit;
   a blower;
   a filter transfer device operable to robotically transfer a filter between a first position for coupling with the suction unit and a container, which contains the examination objects and a solution, and a second position for coupling with the blower-unit; and
   at least one controller programmed to cause the apparatus to:
      perform a blowing process to move the examination objects away from a cap filter of the container to spread the examination objects in the solution prior to collecting the examination objects along a collection surface of the filter,
      perform a suction process, using the suction unit, to draw solution and at least some of the examination objects through the cap filter such that the examination objects are collected along the collection surface of the filter at the first position,
      cause the apparatus to robotically move the filter, which is carrying the examination objects on the collection surface, away from the container and then perform a solution removal process by sucking solution out of the filter, and
      perform a transfer process, using the blower-unit, by delivering air through the filter at the second position to cause the examination objects to be transferred from the collection surface to a surface of a slide.

8. The apparatus of claim 7, wherein the at least one controller is further programmed to
   terminate the suction process after the examination objects have been collected on the collection surface.

9. The apparatus of claim 7, wherein the filter has a collection film with the collection surface, wherein the at least one controller is programmed to cause the blower to blow air through the filter to cause the collection film to bulge toward the slide.

10. The apparatus of claim 7, wherein the at least one controller is programmed to start the suction process while the examination objects are spread in the solution due to the blowing process.

11. An apparatus for handling examination objects, the apparatus comprising:
   a container holder;
   a suction unit;
   a blower;
   a filter transfer device operable to robotically transfer a filter between a first position for coupling with the suction unit and the container, which contains the examination objects and a solution, and a second position for coupling with the blower; and
   at least one controller programmed to cause the apparatus to:
      perform a blowing process to move the examination objects away from a cap filter of the container to, spread the examination objects in the solution prior to collecting the examination objects along a collection surface of the filter, perform a suction process, using the suction unit, to draw solution and at least some of the examination objects through the cap filter such that the examination objects are collected along the collection surface of the filter at the first position, robotically move the filter, carrying the examination objects on the collection surface, away from the container, after robotically moving the filter away from the container, causing the suction unit to suck solution from the filter while the filter carries the examination objects, and causing, via the blower, the examination objects to be transferred from the collection surface to a surface of a slide.

* * * * *